| United States Patent [19] | [11] Patent Number: 4,807,609 |
| --- | --- |
| Meals | [45] Date of Patent: Feb. 28, 1989 |

[54] HAND-FOREARM SUPPORT

[75] Inventor: Roy A. Meals, Los Angeles, Calif.

[73] Assignee: LMB Hand Rehab Products, Inc., San Luis Obispo, Calif.

[21] Appl. No.: 53,632

[22] Filed: May 26, 1987

[51] Int. Cl.⁴ ............................................. A61F 5/04
[52] U.S. Cl. .................................. 128/87 R; 128/77; 128/87 A; 128/88
[58] Field of Search .............. 128/77, 87 C, 88, 87 A, 128/87 R

[56] References Cited

U.S. PATENT DOCUMENTS

| 1,768,770 | 7/1930 | Kettelkamp | 128/88 |
| 2,832,334 | 4/1958 | Whitelaw | 128/77 |
| 3,256,880 | 6/1966 | Caypinar | 128/88 |
| 3,472,224 | 10/1969 | Ewerwahn | 128/87 |

Primary Examiner—Robert A. Hafer
Assistant Examiner—Michael Brown
Attorney, Agent, or Firm—George F. Bethel; Patience K. Bethel

[57] ABSTRACT

A hand-forearm support comprises a generally upright forearm support member having a peripheral wire framework with a soft, flexible material suspended within at least a portion of its framework, a generally horizontal humerus support member having a peripheral wire framework with a soft, flexible material suspended within at least part of its framework, and a base member having two substantially opposed legs. Strap means are employed to secure the forearm support member and the humerus support member to the base member.

5 Claims, 3 Drawing Sheets

HAND-FOREARM SUPPORT

BACKGROUND OF THE INVENTION

1. Field of the Invention

This invention relates to the field of orthopedics and surgery and particularly to a hand-forearm support for use on patients particularly after hand surgery, as well as after trauma and burns.

2. Description of the Prior Art

It is well recognized among orthopedic surgeons as well as other doctors that it is desirable to elevate the hand and forearm after surgery or trauma in order to promote venous return and avoid edema. In the past, this has been accomplished by means of stacked bed pillows and sometimes restrictive slings requiring complicated apparatus which severely limits movement and vision of the patient.

More recently, there has been available a box-like device constructed of medium density, fire-retardant foam, and which is capable of being used by a patient in the supine, prone, or seated position. This device, shown in U.S. Pat. No. Des. 247,311, is still rather large in size as well as bulky and relatively heavy. For this reason it is not particularly suitable for use by ambulatory patients desiring to return to work in the instance that the affected hand is not required for work. Also, this device does not permit the circulation of air completely around the affected limb. As a consequence, it can be uncomfortably hot during use and moist dressings never can dry. Furthermore, it cannot easily be carried around by a patient while walking, due to the size and bulkiness of the device.

The hand-forearm support of the present invention provides significant advantages over the above described device. It is designed to avoid all pressure problems which might occur during its use. The device is also designed to avoid elbow immobilization which adds to its comfort during use. At the same time, it holds the forearm and hand in a naturally supported anatomical position with the aid of straps preferably having Velcro (R) fasteners.

The hand-forearm support is purely functional. It is extremely light in weight, being formed preferably of an outline wire frame covered with an open mesh sleeve of material. This arrangement provides ventilation to all sides of the arm and hand. It is extremely light in weight and small in size. These desirable characteristics permit the device to be used while walking, sitting, or lying down.

While sitting, the support must rest on a surface such as a table in order to elevate the forearm and hand. The exact height can be adjusted with props such as books if needed. The support does not elevate the forearm and hand while walking, but its light weight and compact design permit the patient to easily change location by walking while holding the forearm and hand elevated with the support attached.

An additional advantage is that the base which is very slim fits under the body when the patient is in a reclining position. This permits much more comfortable sleeping since the hand-forearm support permits more freedom of body movement than prior art devices and allows positioning of the arm next to the body.

The sleeve materials can be easily removed and washed when desired. Furthermore, the entire device can be disassembled and placed in a substantially flat position when not in use. This is an advantage not only for storage but also for shipping.

In addition to its use after hand surgery and trauma or burns, the hand-forearm support can also be used after arm, wrist, or shoulder surgery, during mastectomy recovery, during renal dialysis, and during IV infusion.

If desired, it can be used in conjunction with a prop to raise the level of the arm. Its low profile permits working in a seated position without substantially restricting vision over the device. That, coupled with the other stated advantages, will in many instances permit a patient to return to work.

SUMMARY OF THE INVENTION

The hand-forearm support of the invention is comprised of two substantially elongated peripheral or outline framework members which are secured to a base member. The framework members are joined in such a way as to provide substantially a right angle between them. Each of the frame members is covered with a removable sleeve of preferably open mesh material to which are attached straps, preferably of brushed loop material and Velcro (TM) hooks. The straps are employed to secure and to hold the hand and forearm in place within the angle formed by the elongated members.

The elongated members include a generally upright forearm member for support of the forearm and hand, and a generally horizontal humerus member for support of the arm.

The forearm support member and the humerus support member are secured to a base member which is comprised preferably of a length of steel wire, each end of which is bent back upon itself and inserted into a disk, preferably made of machined aluminum. The ends of each of the frame members are also inserted into a disk, preferably made of aluminum. The three disks including the disk attached to the base member and each of the frame members are detachably united by means of a screw fitting which is inserted into an axial internally threaded aperture in each of the solid disks.

Rotation around the screw fitting is prevented by means of an off-center projection attached to the last of the three disks which fits into aligned apertures in the adjacent disks. Each of the wires comprising the base and the framework members are inserted into each of the respective disks, preferably at an angle of approximately 45° which, it is believed, adds stability and avoids turning of the respective members as would be the case if, for example, a 90° angle were employed.

Preferably, the forearm support and humerus support frameworks are comprised of 9 gauge galvanized steel wire and the base member is 9 gauge stainless wire which, during use, provides a slight spring to the wrist area.

DESCRIPTION OF THE DRAWINGS

The invention will be more readily understood by reference to the drawings taken with the accompanying description in which.

DETAILED DESCRIPTION OF THE DRAWINGS

Figure 1:
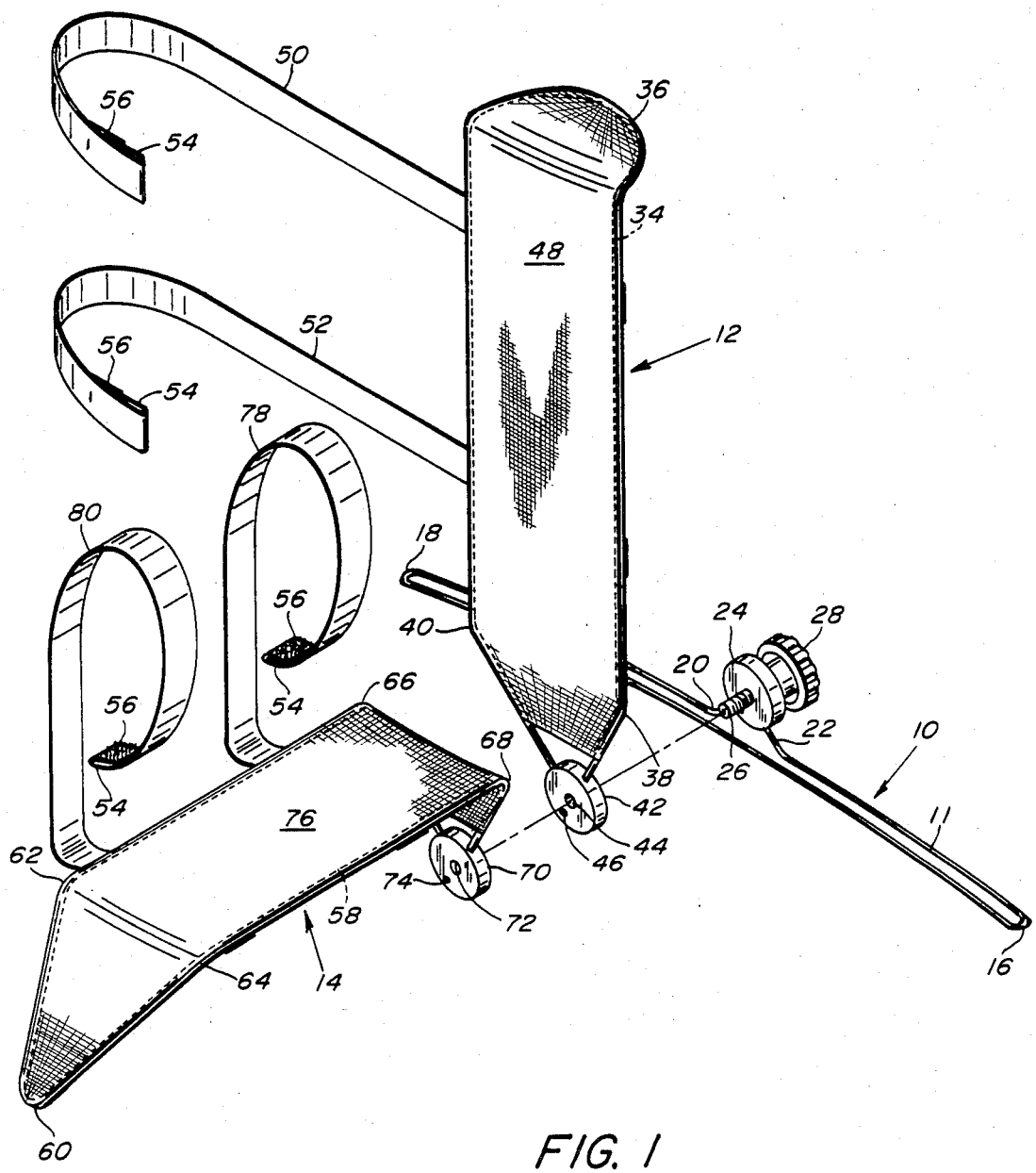
FIG. 1 shows a perspective exploded view of the three major parts of the splint.

Referring now to FIG. 1 there can be seen the three major components of the hand-forearm support of the invention. These include the base member 10, the forearm support member 12, and the humerus support member 14.

The patient contact surfaces of the forearm support member 12 and of the humerus support member 14 form an included angle which lies within the natural bending arc of the elbow of a human being. As a practical matter the preferred range would lie within about 30° to about 130°. Most preferably the included angle would be about 90° for most types of conditions to be treated. The exact angle would depend upon the injury but in any event would desirably promote venus return and avoid edema.

As used herein and in the appended claims, the term "distal" is meant distal to the apex of the included angle. Similarly, the term "proximal" is meant proximal to the apex of the included angle.

Figure 2:
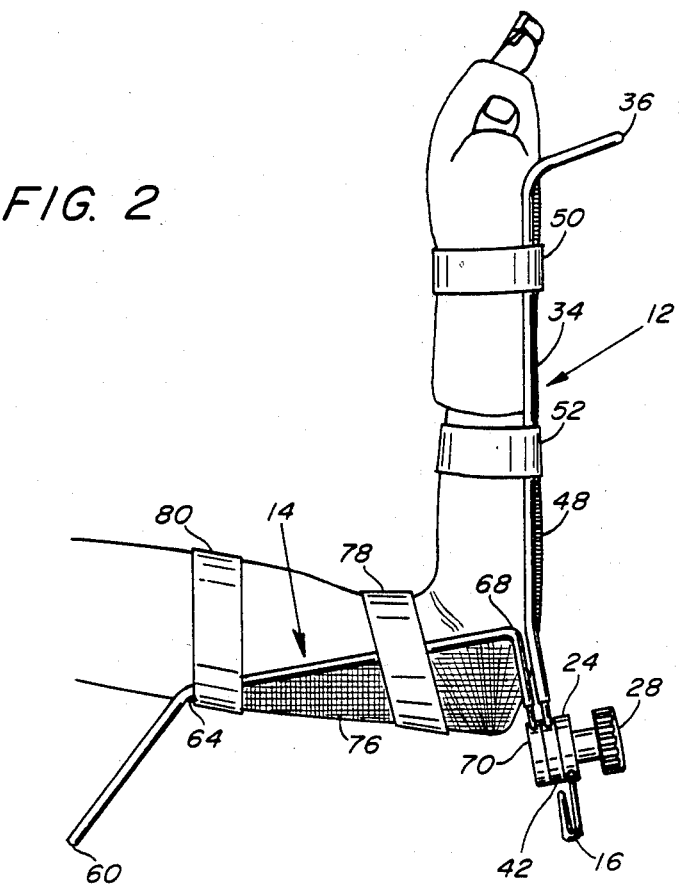
FIG. 2 shows a side view of the splint illustrating its use.
Figure 3:
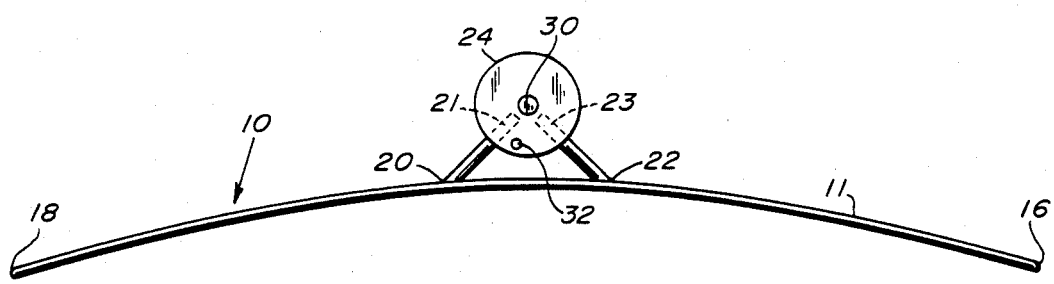
FIG. 3 shows a front elevation view of the base member.

The base member 10 shown in FIGS. 1, 2, and 3 is preferably formed of a continuous length of heavy gauge steel wire, each end being first bent upon itself to form two narrow loops 16 and 18 respectively and then at a point substantially midway between loops 16 and 18 being bent upwardly at an angle of substantially 45° as indicated at 20 and 22. The ends of the wire 11 are inserted into disk 24, preferably of aluminum, at an angle of approximately 45°. The disk 24 contains radially oriented bores 21 and 23 shown in outline in FIG. 3 for the reception of the ends of the wire 11. In addition, the disk 24 is internally threaded at its axial center 30 for reception of an externally threaded screw member 26 having an attached handle 28 for grasping.

As best seen in FIG. 3, the base member 10 has a slightly arched configuration providing additional strength to the hand-forearm support as a whole.

The internally threaded axial opening 30 in disk 24 can also be seen in FIG. 3. In addition, there is shown an aperture 32 which is spaced from and parallel to the axial center of the disk 24. The bores 21 and 23 for the reception of the ends of the base member wire 11 extend radially through the disk 24.

Figure 4:
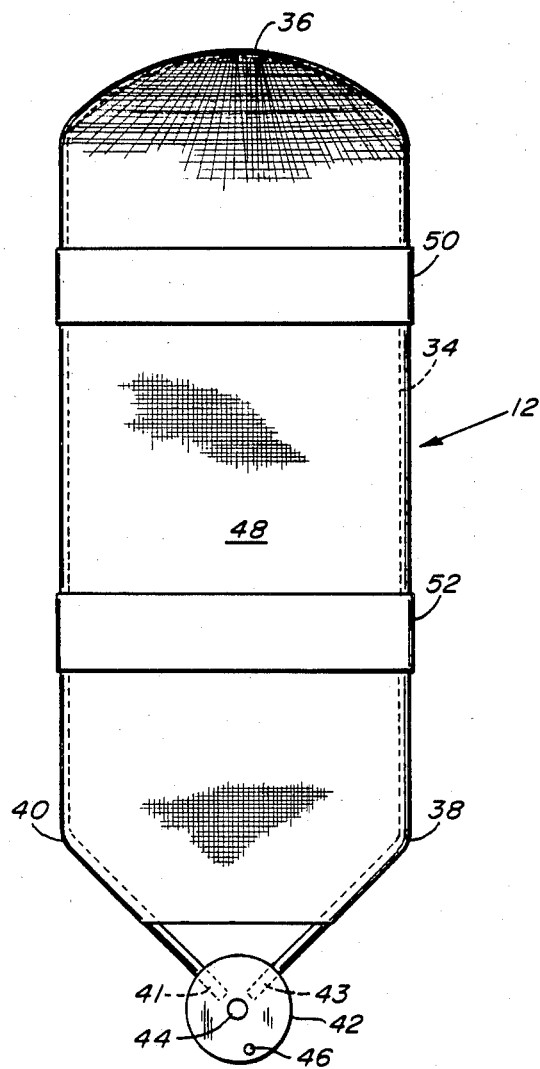
FIG. 4 shows a front elevation view of the forearm support member.
Figure 5:
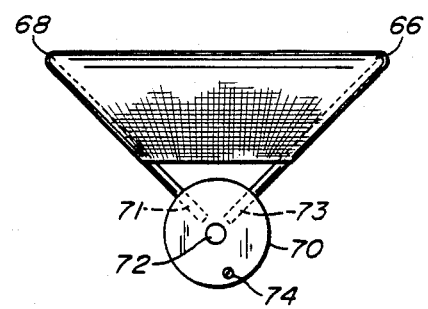
FIG. 5 shows a front elevation view of the humerus support member.
Figure 6:
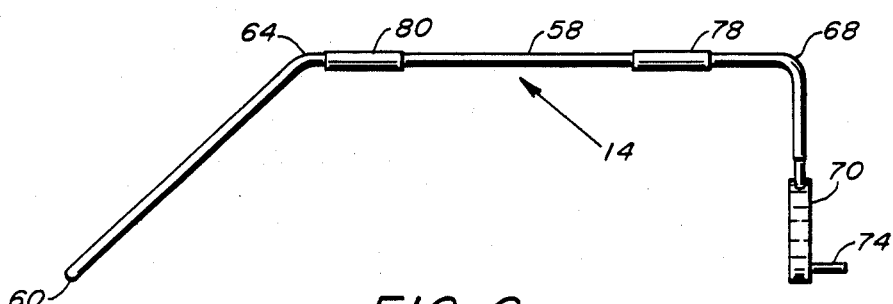
FIG. 6 shows a side elevation view of the humerus support member.

The forearm support member 12 shown in FIGS. 1, 2, and 4 has an elongated generally upright rectangular configuration. It includes an outline peripheral framework 34 shown in outline. The framework 34 is preferably formed of a single piece of stainless steel. The distal end rounded end of the substantially elongated framework 34 is bent away from the interior portion of the splint as shown at 36 to an angle of approximately 45°. Since the purpose of the bending of the upper framework area 36 of the forearm support member 12 is to avoid contact of the framework 34 with any portion of the hand-wrist area, the exact angle is not critical. When a sleeve of material 48 encloses the framework 34 a resilient cushioning effect is achieved.

The proximal free ends of the framework 34 of forearm support member 12 are bent toward each other to approximately a 45° angle relative to the vertical as indicated at 38 and 40 for insertion into a disk 42, preferably of aluminum. The disk 42 is provided with radially oriented bores 41 and 43 shown in outline for receiving the proximal ends of the framework 34. In addition, the disk 42 contains an internally threaded axial hole 44 and an off-center hole 46 which is parallel to the axial center of the disk.

As noted above, the framework 34 is enclosed by a sleeve member 48 comprised preferably of a lightweight, open mesh stretchy material which can be removed as desired. Attached to the sleeve 48 are straps 50 and 52.

The straps are preferably composed of a foam cushion material having an exterior brushed surface and an interior, smooth knit surface. The free end of each strap is preferably folded over as indicated at 54 in FIG. 1 and a patch of nylon hooks are attached thereto as indicated at 56. The strap can be attached to the sleeve material by any convenient means such as by stitching or stapling but is preferably glued to the sleeve material. The strap is easily secured with one hand by encircling the forearm and attaching it to itself to the exterior brushed area by means of the hooked area 56. Strap 52 operates in the same manner.

As shown in FIGS. 1, 2, 5, and 6 the humerus support member 14 of the hand-forearm support is comprised of an elongated generally horizontal member. The humerus support member 14 includes a peripheral framework 58 shown in outline which is preferably formed of a single length of stainless steel. The distal end 60 of the elongated outline framework 58 has a generally triangular configuration which has been bent downwardly away from the generally horizontal plane of the arm support member 14 at points 62 and 64.

The triangular bent-away portion of distal end 60 not only avoids contact of the framework 58 with the upper arm of a patient and increases the resiliency of the splint, but also in cooperation with the two points 16 and 18 of the base member 10 provides a stable condition to the stand. A square or rounded configuration can be used as well.

The proximal free ends of the framework 58 are bent at points 66 and 68 to an angle preferably of approximately 90° relative to the longest parallel section of the splint and at the same time are bent toward each other preferably to an angle of approximately 45° relative to the vertical.

The proximal free ends are inserted into a disk 70, preferably of aluminum, having radially oriented bores 71 and 73 for receiving the ends of the framework 58. The included angle is the same as the angle at which the ends 66 and 68 are bent toward each other and is preferably about 45°. The disk 70 also includes an internally threaded axial aperture 72 and an off center cylindrical projection 74 parallel to the axial aperture 72 and of a diameter designed to fit into apertures 46 and 32 of forearm member 12 and base member 10 respectively. This can be seen in FIG. 6.

When all of the pieces are connected as shown in FIG. 2, the projection 74 prevents the respective members 10, 12, and 14 which are secured to disks 24, 42, and 70 respectively from rotating with respect to each other. This arrangement effectively stabilizes the hand-forearm support as a whole while at the same time keeping the support light in weight and resilient.

The humerus support member 14 also includes an open mesh sleeve member 76, preferably of an open mesh stretchy material having attached straps 78 and 80 which operate exactly ad described for straps 50 and 52. In place of the sleeve material 48 and 76 there can be employed netting, lacing, or other natural or synthetic cloth or cloth-like materials. Strong flexible materials such as fiber reinforced paper can also be employed.

The disks and the base member do not contact the hand, forearm, elbow or humerus during use. The forearm and arm rest on and are supported by the material 48 and 76 suspended between frameworks 34 and 58 respectively.

An additional feature of the invention not mentioned above includes the fact that the exteriorly threaded screw member 26 having the knob or handle 28 attached thereto preferably contains an unthreaded portion not shown on its shank adjacent the knob 28 so that the threaded area will not cause the entire base member to rotate when the threaded portion 20 is being inserted into the respective interiorly threaded axial holes 44 and 72 of disks 42 and 70 respectively.

The splint thus described provides a lightweight, easily assembled strong hand-forearm support which holds the hand and forearm in an elevated position, accommodating the natural bend of the elbow and at the same time avoiding any pressure points. The use of steel for the framework of the forearm support member 12 and the humerus support member 14 gives a springy resistance to the wrist and elbow. Similarly, the bent-away portion 36 avoids pressure contact with the hand on the forearm support member 12. At the same time the bent-away portion 60 of the humerus support member 14 avoids pressure against the upper arm and the bent-away portion of humerus support member 14 at points 66 and 68 avoids pressure against the elbow.

While it is contemplated and preferred that the framework of each of the major support members 10, 12 and 14 be formed of steel, other materials can also be used in place thereof. Similarly, while the disks are formed of aluminum, other materials can be used in place thereof, including for example other metals or plastics such as nylon, and fiber glass reinforced plastic and composites. Examples of such materials include but are not limited to other metals, plastics, wood, and combinations and composites of such materials.

Various modifications of the invention are contemplated and can be resorted to by those skilled in the art without departing from the spirit and scope of the invention as defined by the following appended claims.

I claim:

1. A freestanding hand-forearm support for elevation of a hand above the level of the elbow comprising:
   a forearm support member, a humerus support member, and a base member;
   said hand-forearm support having an interior as defined by the surfaces of said forearm support member and said humerus support member which contact the arm and forearm of a patient and which define an included angle which is within the natural bending arc of the elbow of a human being;
   said forearm support member being generally upright and having a peripheral framework comprised of a single continuous length of wire with a flexible material suspended within at least a portion of said framework;
   said forearm support member comprising a distal portion which is distal to the apex of said included angle, a central body portion, and a proximal portion which is proximal to the apex of said included angle, said central portion including spaced apart generally parallel wire extensions joined in said distal portion, said distal portion being angled away from the interior of the hand-forearm support and said proximal portion including means for attachment to said base member comprising the free ends of the wire extending toward each other at substantially 45° which are anchored in said base member attachment means;
   said humerus support member being generally horizontal and having a peripheral framework comprised of a single continuous length of wire, and a flexible material suspended within at least part of said framework;
   said humerus support means comprising a distal portion which is distal to the apex of said included angle, a central body portion, and a proximal portion which is proximal to the apex of said included angle, said central portion comprising spaced apart generally parallel wire extensions joined in said distal portion, said distal portion being angled away from the interior of the hand-forearm support and said proximal portion including means for attachment to said base member comprising the free ends of the wire extending toward each other at substantially 45° which are anchored in said base member attachment means;
   said base member comprising a pair of legs formed of a single continuous length of wire bent back on itself, the free ends of which are secured to said attachment means at a point substantially midway between said legs;
   attachment means for securing said forearm support member and said humerus support member to said base member comprising three separate disks, one disk being attached to each of said forearm support member, to said humerus support member, and to said base member;
   means for detachably securing said disks together;
   said humerus support member being secured to a disk having an internally threaded axial hole and having a pair of radial bores into which are inserted the free ends of the proximal portion of said wire framework;
   said forearm support member being secured to a disk having an internally threaded axial bore and having a pair of radial bores into which are inserted the free ends of the proximal portion of said wire framework;
   said base member further comprising a disk having an internally threaded axial hole and having a pair of radial bores for receiving and holding the free ends of the base member wire;
   an externally threaded shaft member for threading through the respective internally threaded axial holes of the disks of said base member, said forearm support member and said humerus support member to secure said forearm support member, said humerus support member, and said base member together.

2. A freestanding hand-forearm support as claimed in claim 1 wherein:
   said flexible material suspended within said forearm support member and said humerus support member is comprised of a sleeve of fabric substantially enclosing each said framework.

3. A freestanding hand-forearm support as claimed in claim 2 wherein:
   said fabric is a stretchy open mesh fabric.

4. A freestanding hand-forearm support as claimed in claim 1 further comprising:

an off center projection on said forearm support member disk which projection extends parallel to said axis of said disk;

an off center aperture on said humerus support member disk which aperture is aligned with said projection on the disk of said arm support member; and, an off center aperture on said base member disk which aperture is parallel to said axial hole and aligned with said aperture and said projections respectively of the disks of said forearm support member and said humerus support member so that said disks are prevented from rotation with respect to each other.

5. A freestanding hand-forearm support as claimed in claim 4 wherein:

said pair of radially oriented bores in each of said disks are separated by an arc radian of approximately 45°.

* * * * *